United States Patent [19]

Turnbull et al.

[11] Patent Number: 4,487,801
[45] Date of Patent: Dec. 11, 1984

[54] FRAGRANCE-RELEASING PULL-APART SHEET

[75] Inventors: Everett M. Turnbull, Hastings, Minn.; Jack W. Charbonneau, Sommerset, Wis.

[73] Assignee: Minnesota Mining and Manufacturing Company, St. Paul, Minn.

[21] Appl. No.: 540,501

[22] Filed: Oct. 11, 1983

[51] Int. Cl.³ .................. B32B 5/16; B32B 29/04
[52] U.S. Cl. ........................ 428/313.5; 229/68 R; 428/323; 428/327; 428/905
[58] Field of Search ........... 428/323, 327, 396, 313.5, 428/905; 252/315.1, 522 K, 522 A; 424/37

[56] References Cited

U.S. PATENT DOCUMENTS

| | | | |
|---|---|---|---|
| 3,016,308 | 1/1962 | Macaulay | 117/36.7 |
| 3,516,941 | 6/1970 | Matson | 252/316 |
| 3,623,659 | 11/1971 | Malerson et al. | 428/905 |
| 4,058,434 | 11/1977 | Vincent et al. | 162/165 |
| 4,186,743 | 2/1980 | Steiger | 428/905 |
| 4,201,404 | 5/1980 | Charbonneau et al. | 282/27.5 |
| 4,251,386 | 12/1981 | Saeki et al. | 252/316 |

FOREIGN PATENT DOCUMENTS 1156725 7/1969 United Kingdom.

*Primary Examiner*—Paul J. Thibodeau
*Attorney, Agent, or Firm*—Donald M. Sell; James A. Smith; Mark A. Litman

[57] ABSTRACT

Microcapsules containing material therein can be burst to release the encapsulated material when the capsules are contained in an adhesive securing two surfaces together and the surfaces are pulled apart.

20 Claims, No Drawings

FRAGRANCE-RELEASING PULL-APART SHEET

FIELD OF THE INVENTION

This invention relates to microencapsulated materials, articles containing microencapsulated materials and the method of preparing such articles. In particular, the present invention relates to microencapsulated materials adhesively secured between two temporarily adhered surfaces such that upon separation of said two surfaces, the capsules rupture, releasing material contained therein.

BACKGROUND OF THE INVENTION

Encapsulated materials have been used for many years in a wide variety of commercial applications. Early uses of encapsulated materials included paper coated with capsules bearing coloring material therein which could be used as a recording medium. U.S. Pat. No. 3,016,308 discloses one of the early efforts using encapsulated material as the image source on recording paper. U.S. Pat. Nos. 4,058,434 and 4,201,404 show other methods of application of encapsulated coloring materials on paper substrates to be used as imaging media and the like. U.S. Pat. No. 3,503,783 shows microcapsules having coloring material therein which are ruptureable by the application of heat, pressure and/or radiation because of a metal coating on the surface of the capsule. These ruptureable microcapsules, in one embodiment, may be secured between a substrate and a photoconductive top coat to enable photosensitive imaging of the system.

A wide variety of processes exist by which microcapsules can be manufactured. These varied processes provide different techniques for producing capsules of varying sizes, alternative materials for the composition of the capsule shell and various different functional materials within the shell. Some of these various processes are shown in U.S. Pat. Nos. 3,516,846; 3,516,941; 3,778,383; 4,087,376; 4,089,802; 4,100,103 and 4,251,386 and British patent specification Nos. 1,156,725; 2,041,319 and 2,048,206. A wide variety of different materials may also be used in making the capsule shells. A popular material for shell formation is the polymerization reaction product between urea and formaldehyde or melamine formaldehyde, or the polycondensation products of monomeric or low molecular weight polymers of dimethylolurea or methylolated urea with aldehydes. A variety of capsule forming materials are disclosed, for example, in U.S. Pat. Nos. 3,516,846 and 4,087,376 and U.K. patent specification Nos. 2,006,709 and 2,062,570.

As shown in these references, the principal utility of microencapsulated materials is in the formation of a surface coated with the microcapsules in a binder. The microcapsules are ruptured by various means to release the material contained therein. In addition to release of physically observable materials such as ink in order to form a visible image, other types of active ingredients such as odor releasing materials, bacteriostatic materials, chemically active materials and the like have been provided in this manner.

SUMMARY OF THE INVENTION

The present invention relates to a new article containing ruptureable microcapsules. The novel article comprises two sheets of material which are temporarily bonded by means of an adhesive with ruptureable microcapsules dispersed therein. The microcapsules are ruptured by pulling apart the sheets which causes the capsules to rupture and release the ingredients contained therein. By selecting the relative physical properties of the sheet, adhesive, capsules and the binding forces amongst them, a high rate of capsule rupturing can be obtained consistently.

DETAILED DESCRIPTION OF THE INVENTION

The present invention relates to an article comprising at least two sheets temporarily secured by means of a adhesive layer having microcapsules dispersed therein. The sheet materials may effectively be of any composition such as paper, polymeric film, fabric, foil and the like. These sheets may be flexible or rigid, but generally flexible sheets such as paper or coated paper are preferred. The binder material must form a bond to the sheets which is stronger than the cohesive strength of the adhesive with the capsules dispersed therein. Although it is generally desirable to have an adhesive, the cohesive strength of which is less than its adhesive strength to the cover sheets, this is not essential. When capsules are included within the adhesive composition, the effective cohesive strength of the adhesive tends to be reduced. Adhesives, which by themselves would cause the sheets to be damaged during separation, can be used in combination with capsules in the practice of the present invention because of lowered effective cohesive strength. The capsules in the present invention may comprise any ruptureable capsule containing an active ingredient therein. The tensile rupture strength of the capsules must be less than the cohesive tensile strength of the binder used. It has also been found that the size of the capsules plays an important role in the usefulness of capsules within ruptureable sheets according to the practice of the present invention. Generally the capsules must have an average diameter between 12 and 30 microns when the capsule payload is between 80 and 90% by weight of the total capsule weight. It is highly preferred that the capsules have an average diameter between 14 and 26 microns and it is most preferred that the capsules have a diameter between 15 and 25 microns. These dimensions play a surprisingly important role in the ability to control the percentage of rupture of capsules in the practice of the present invention. With lower payloads (e.g., 70–80%), the capsules should be larger to provide the necessary rupture strength. The broadest range of capsule size under any conditions would be about 8 to 30 microns, with 8 micron capsules used with a 90–95% by weight payload.

It has been found that a relationship exists amongst the factors of peel force, adhesive coating weight and the median capsule diameter. This relationship can be expressed as $P = k(C_w/d^2)$, wherein $P$ equals the peel force, $C_w$ equals the adhesive line coating weight, $d$ equals the median diameter of the capsules and $k$ equals a co-efficient relating to binder and substrate properties. The peel force should be in the range of 1.5 to 28 ounces per inch, preferably 1.5 to 8.0 ounces per inch. The coating weight of adhesive and microcapsules should be at a coating weight of approximately one pound for 300 to 800 square feet. Preferably the coating weight should be between approximately one pound for each 400 to 650 square feet. At higher coating weights, the surface of the cover sheets tend to tear, while at lower coating weights, the sheets tend to pull apart and the adhesive tends to rupture in advance of the capsules included therein. The capsules should form between 20 and 90 percent by volume of the total adhesive composition, and preferably between 50 and 85 percent of the total composition volume.

The nature and composition of the adhesive binder is not critical to the practice of the invention as long as the required adhesive and cohesive properties are met. The adhesive may be pressure sensitive, solvent sensitive or thermally activatable. It is generally prefered that the adhesive be activatable by a solvent or heat because the desired physical properties are more readily obtained in those classes of adhesives. There is also no need for rejoining the sheets after rupturing of the capsules and so the pressure sensitive function is not necessary.

The adhesive (with microcapsules) may be applied between two separate sheets in either a continuous or discontinuous patterns. It is usually desirable to leave at least some portion of at least one outer edge of the sheets unbonded so as to provide an area where separation can be easily started. A single sheet may be folded so as to form two facing sheets joined along one edge. The adhesive may be applied on the interior area adjacent the fold. This provides a folded article that can be readily opened, rupturing the capsules, yet leaves a single artifact rather than two sheets after use.

It is preferred that the coated inside portion of the single sheets (e.g., from the fold to the end of the adhesive) constitute from 5 to 40% of the surface area of the sheets. In two sheet constructions, 10 to 95 percent binder coverage is used. Some uses may allow for only a single corner to be uncoated so as to provide a starting point for the separation of the sheets, but the 5 to 40% range is preferred with 10 to 30% more preferred.

Any class of adhesives including but not limited to polyurethanes, polyacrylates, polyvinyl resins, polyamides, polyesters, polyolefins, starches, gum arabic, gelatin and the like may be readily used in the practice of the present invention.

In effect, to best practice the present invention it is desirable that certain properties within the article have relative values for each of the materials used. The cohesive strength of the sheet material should exceed the adhesive strength between the binder and the sheet. The adhesive strength of the binder to the sheet should exceed the cohesive strength of the binder and capsules therein. The cohesive strength of the binder should exceed the tensile rupture limits of the capsules.

As previously noted, the size of the capsules has an important effect upon the practice of the present invention. With capsules less than 12 microns, there is so little rupturing of the capsules as to prevent the useful release of materials. Above 30 microns, the particles are so large that they are readily burst by handling of the sheets and manufacturing procedures. Furthermore, with the large size particles it is extremely difficult to control bursting upon separation of the sheets because of increased effects upon adhesive and cohesive properties of materials in contact with the capsules. The preferred range of 15 to 25 microns is important to the practice of the present invention. Within these limits, rupture in excess of 50 percent of the particles can be easily obtained. Rupture in excess of 80 percent of the capsules can usually be accomplished in the practice of the present invention within those limits.

The capsules may contain a wide variety of active materials therein. The least useful of materials to be included therein would be coloring agents since separation of the sheets would generally produce uniform coloration rather than a distinct image. The most preferred types of ingredients would be fragrant materials or materials which provide chemically active vapors or liquids. These may or may not also be colored. For example, a testing kit for the presence of chemical vapors could be produced by providing material within the capsules which would react in the vapor phase with the material for which a leak is being investigated. By separating the sheet, rupturing the capsules and exposing the vapor test material, a color forming reaction in the air or on the sheet could be really observable. Another particularly useful format would be to include the microcapsules within a water-remoistenable adhesive and to use the mixture as the binding adhesive for novelty envelopes. For example, the microcapsules could contain the aromatic essence of baby oil, cake or pizza for invitation envelopes for a baby shower, wedding (or birthday party), or general party, respectively.

This invention may be practiced with a number of various modifications that provide new and useful articles and processes. For example, the adhesive composition with capsules may be associated with various printed formats to form novelty items. The exterior sheets or exposed inner face of the sheets may have questions or stories or rhymes, and under the adhesive may be a printed picture answering the question, depicting the story or completing the rhyme, with the released fragrance emphasizing the picture further.

The capsule bearing adhesive layer in the construction of the present invention may also be used for a security device. In an article such as a coupon, lottery ticket or gaming card, the important display could be located under the adhesive. Once the article had been opened and the fragrance released, any subsequent recipient would be aware of its prior use and could be apprised of the possibility of tampering. The adhesive being nonpressure sensitive, it is not repositionable, the sheets are not easily rebonded, and there would be no release of fragrance if the sheets were rebonded with additional non-fragranced adhesive and reopened. The absence of fragrance would indicate that the article had been tampered with.

These and other aspects of the present invention will be shown in the following examples.

EXAMPLE

An oil having the aroma of Concord grapes was encapsulated in a urea-formaldehyde resin made according to the process of Example 20 of U.S. Pat. No. 3,516,941. The capsules had an average diameter of about 17 micrometers and an estimated payload of 85% by weight (ratio of oil to total capsule weight).

A coating formulation was prepared comprising 64 parts capsules, 35 parts polyvinyl alcohol and 1 part glycerine (plasticizer) in a water slurry. This formulation was coated at 4.5 lbs. per 1300 sq. ft. (dry weight) onto coated paper base stock. The coating was made in a stripe down the middle of the paper and the paper folded sharply around the stripe after coating. The coated and folded paper was air dried at ambient conditions for two days.

Sections of the coated paper were cut to provide a folded sheet with a 20% portion of the paper extending from the fold coated with adhesive and capsules. The edges of the sheets were grasped by hand and pulled open sharply. There was a burst of grape aroma after the interior adhesive strip was ruptured.

We claim:

1. A device for exposing a liquid to the atmosphere so as to enable said liquid to react, or at least partially evaporate, said device comprising
   (1) at least two sheets bound by a single layer of a non-pressure sensitive adhesive composition layer,
   (2) said adhesive composition layer containing microcapsules with said liquid within the shell of the microcapsules, and
   (3) said microcapsules having an average diameter between 8 and 30 micrometers, the cohesive strength of the adhesive composition layer being less than the strength of the bond between said adhesive composition and said sheets, and the tensile rupture strength of said microcapsules being less than the cohesive strength of the adhesive composition.

2. The device of claim 1 wherein said sheets are flexible sheets.

3. The device of claim 2 wherein said flexible sheets are selected from the group consisting of paper and polymeric film.

4. The device of claim 1 wherein said microcapsules have an average diameter between 12 and 30 micrometers.

5. The device of claim 2 wherein said microcapsules have an average diameter between 14 and 26 micrometers.

6. The device of claim 3 wherein said microcapsules have an average diameter between 14 and 26 micrometers.

7. The device of claim 1 wherein said microcapsules comprise gelatin and are between 35 and 60% by volume of said adhesive composition.

8. The device of claim 3 wherein said microcapsules comprise between 50 and 85% by volume of said adhesive composition.

9. The device of claim 4 wherein said microcapsules comprise between 50 and 85% by volume of adhesive composition.

10. The device of claim 6 wherein said microcapsules comprise between 50 and 85% by volume of said adhesive composition.

11. The device of claim 1 wherein said liquid is an odor releasing material and the shell of said microcapsule comprises a urea-formaldehyde resin.

12. The device of claim 2 wherein said liquid is an odor releasing material.

13. The device of claim 3 wherein said liquid is an odor releasing material.

14. The device of claim 4 wherein said liquid is an odor releasing material.

15. The device of claim 6 wherein said liquid is an odor releasing material.

16. The device of claim 8 wherein said liquid is an odor releasing material.

17. The device of claim 3 wherein said adhesive is a water-remoistenable adhesive.

18. The device of claim 6 wherein said adhesive is a water-remoistenable adhesive.

19. The device of claim 13 wherein said adhesive is a water-remoistenable adhesive.

20. The device of claim 19 wherein said sheets comprise overlying portions of an envelope.

* * * * *

Dedication 4,487,801.—*Everett M. Turnbull*, Hastings, Minn; and *Jack W. Charbonneau*, Sommerset, Wis. FRAGRANCE-RELEASING PULL-APART SHEET. Patent dated Dec. 11, 1984. Dedication filed Jan. 30, 1989, by the assignee, Minnesota Mining and Manufacturing Co.

Hereby dedicates to the public the remaining term of said patent.

[ *Official Gazette June* 6, 1989 ]